United States Patent
Ayal et al.

(10) Patent No.: US 7,324,853 B2
(45) Date of Patent: Jan. 29, 2008

(54) NERVE STIMULATION FOR TREATING SPASTICITY, TREMOR, MUSCLE WEAKNESS, AND OTHER MOTOR DISORDERS

(75) Inventors: Shai Ayal, Jerusalem (IL); Ehud Cohen, Ganei Tikva (IL); Ron Dabby, Raanana (IL)

(73) Assignee: Biocontrol Medical Ltd., Yehud (IL)

( * ) Notice: Subject to any disclaimer, the term of this patent is extended or adjusted under 35 U.S.C. 154(b) by 483 days.

(21) Appl. No.: 10/981,939

(22) Filed: Nov. 5, 2004

(65) Prior Publication Data

US 2005/0102007 A1 May 12, 2005

Related U.S. Application Data

(63) Continuation-in-part of application No. 10/254,024, filed on Sep. 24, 2002, now Pat. No. 6,892,098, which is a continuation-in-part of application No. 10/205,474, filed on Jul. 24, 2002, now Pat. No. 6,907,295, which is a continuation-in-part of application No. 09/944,913, filed on Aug. 31, 2001, now Pat. No. 6,684,105.

(51) Int. Cl.
*A61N 1/18* (2006.01)
(52) U.S. Cl. .......................... 607/48; 607/45
(58) Field of Classification Search ............. 607/45, 607/48
See application file for complete search history.

(56) References Cited

U.S. PATENT DOCUMENTS

| | | |
|---|---|---|
| 3,411,507 A | 11/1968 | Wingrove |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | van den Honert et al. |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Crish et al. |

(Continued)

FOREIGN PATENT DOCUMENTS

EP 0 688 577 A1 12/1995

(Continued)

OTHER PUBLICATIONS

U.S. Appl. No. 60/263,834, entitled "Selective Blocking of Nerve Fibers", filed Jan. 25, 2001.

(Continued)

*Primary Examiner*—Angela D. Sykes
*Assistant Examiner*—Joseph Stoklosa
(74) *Attorney, Agent, or Firm*—Darby & Darby PC

(57) ABSTRACT

A method for treating spasticity of a subject is provided, including driving a current into a nerve of the subject that includes one or more sensory fibers, and configuring the current so as to inhibit propagation of action potentials in one or more of the sensory fibers, so as to treat the spasticity. In a preferred embodiment, the sensory fibers include one or more Ia sensory fibers, and configuring the current includes configuring the current so as to inhibit propagation of the action potentials in at least one of the Ia sensory fibers.

9 Claims, 7 Drawing Sheets

U.S. PATENT DOCUMENTS

| | | | |
|---|---|---|---|
| 4,628,942 | A | 12/1986 | Sweeney et al. |
| 4,632,116 | A | 12/1986 | Rosen et al. |
| 4,649,936 | A | 3/1987 | Ungar et al. |
| 4,663,102 | A | 5/1987 | Brenman et al. |
| 4,702,254 | A | 10/1987 | Zabara |
| 4,739,764 | A | 4/1988 | Lue et al. |
| 4,867,164 | A | 9/1989 | Zabara |
| 4,926,865 | A | 5/1990 | Oman |
| 4,962,751 | A | 10/1990 | Krauter |
| 5,025,807 | A | 6/1991 | Zabara |
| 5,069,680 | A | 12/1991 | Grandjean |
| 5,178,161 | A | 1/1993 | Kovacs |
| 5,188,104 | A | 2/1993 | Wernicke et al. |
| 5,199,428 | A | 4/1993 | Obel et al. |
| 5,199,430 | A | 4/1993 | Fang et al. |
| 5,203,326 | A | 4/1993 | Collins |
| 5,205,285 | A | 4/1993 | Baker, Jr. |
| 5,215,086 | A | 6/1993 | Terry, Jr. et al. |
| 5,263,480 | A | 11/1993 | Wernicke et al. |
| 5,282,468 | A | 2/1994 | Klepinski |
| 5,292,344 | A | 3/1994 | Douglas |
| 5,299,569 | A | 4/1994 | Wernicke et al. |
| 5,314,495 | A | 5/1994 | Kovacs |
| 5,330,507 | A | 7/1994 | Schwartz |
| 5,335,657 | A | 8/1994 | Terry, Jr. et al. |
| 5,423,872 | A | 6/1995 | Cigaina |
| 5,439,938 | A | 8/1995 | Snyder et al. |
| 5,454,840 | A | 10/1995 | Krakovsky et al. |
| 5,540,730 | A | 7/1996 | Terry, Jr. et al. |
| 5,540,734 | A | 7/1996 | Zabara |
| 5,562,718 | A | 10/1996 | Palermo |
| 5,571,150 | A | 11/1996 | Wernicke et al. |
| 5,634,462 | A | 6/1997 | Tyler et al. |
| 5,690,681 | A | 11/1997 | Geddes et al. |
| 5,690,691 | A | 11/1997 | Chen et al. |
| 5,700,282 | A | 12/1997 | Zabara |
| 5,707,400 | A | 1/1998 | Terry, Jr. et al. |
| 5,711,316 | A | 1/1998 | Elsberry et al. |
| 5,716,385 | A | 2/1998 | Mittal et al. |
| 5,755,750 | A | 5/1998 | Petruska et al. |
| 5,824,027 | A | 10/1998 | Hoffer et al. |
| 5,832,932 | A | 11/1998 | Elsberry et al. |
| 5,833,709 | A | 11/1998 | Rise et al. |
| 5,836,994 | A | 11/1998 | Bourgeois |
| 5,916,239 | A | 6/1999 | Geddes et al. |
| 5,938,584 | A | 8/1999 | Ardito et al. |
| 6,026,326 | A | 2/2000 | Bardy |
| 6,058,331 | A | 5/2000 | King |
| 6,066,163 | A * | 5/2000 | John .......................... 607/45 |
| 6,083,249 | A | 7/2000 | Familoni |
| 6,086,525 | A | 7/2000 | Davey et al. |
| 6,091,922 | A | 7/2000 | Bisaiji |
| 6,091,977 | A | 7/2000 | Tarjan et al. |
| 6,094,598 | A | 7/2000 | Elsberry et al. |
| 6,097,984 | A | 8/2000 | Douglas |
| 6,104,955 | A | 8/2000 | Bourgeois |
| 6,104,960 | A | 8/2000 | Duysens et al. |
| 6,119,516 | A | 9/2000 | Hock |
| 6,146,335 | A | 11/2000 | Gozani |
| 6,169,924 | B1 | 1/2001 | Meloy et al. |
| 6,205,359 | B1 | 3/2001 | Boveja |
| 6,230,061 | B1 | 5/2001 | Hartung |
| 6,266,564 | B1 | 7/2001 | Hill et al. |
| 6,319,241 | B1 | 11/2001 | King et al. |
| 6,341,236 | B1 | 1/2002 | Osorio et al. |
| 6,356,784 | B1 | 3/2002 | Lozano et al. |
| 6,366,813 | B1 | 4/2002 | DiLorenzo |
| 6,405,079 | B1 | 6/2002 | Ansarinia |
| 6,449,507 | B1 | 9/2002 | Hill et al. |
| 6,463,328 | B1 | 10/2002 | John |
| 6,473,644 | B1 | 10/2002 | Terry, Jr. et al. |
| 6,587,727 | B2 | 7/2003 | Osorio et al. |
| 6,600,956 | B2 | 7/2003 | Maschino et al. |
| 6,671,556 | B2 | 12/2003 | Osorio et al. |
| 6,895,280 | B2 | 5/2005 | Meadows et al. |
| 6,928,320 | B2 | 8/2005 | King |
| 2002/0107553 | A1 | 8/2002 | Hill et al. |
| 2003/0040774 | A1 | 2/2003 | Terry et al. |
| 2003/0195574 | A1 | 10/2003 | Osorio et al. |
| 2004/0138721 | A1 | 7/2004 | Osorio et al. |
| 2004/0152958 | A1 | 8/2004 | Frei et al. |
| 2004/0158119 | A1 | 8/2004 | Osorio et al. |
| 2006/0015153 | A1 | 1/2006 | Gliner et al. |
| 2006/0074450 | A1 | 4/2006 | Boveja et al. |

FOREIGN PATENT DOCUMENTS

| | | |
|---|---|---|
| WO | WO-01/10375 A2 | 2/2001 |
| WO | WO-01/10432 | 2/2001 |
| WO | WO-01/26729 | 4/2001 |

OTHER PUBLICATIONS

Ungar, I. J., et al. "Generation of Unidirectionally Propagating Action Potentials Using a Monopolar Electrode Cuff", Annals of Biomedical Engineering, vol. 14, pp. 437-450, 1986.

Sweeney, James D., et al. "An Asymmetric Two Electrode Cuff for Generation of Unidirectionally Propagated Action Potentials", IEEE Transactions on Biomedical Engineering, vol. BME-33, No. 6, Jun. 1986.

Naples, Gregory G., et al. "A Spiral Nerve Cuff Electrode for Peripheral Nerve Stimulation", IEEE Transactions of Biomedical Engineering, vol. 35, No. 11, Nov. 1998, pp. 905-916.

Sweeney, Jamed D., et al. "A Nerve Cuff Technique for Selective Excitation of Peripheral Nerve Trunk Regions", IEEE Transactions on Biomedical Engineering, vol. 37, No. 7, Jul. 1990.

Van Den Honert, et al. "Generation of Unidirectionally Propagated Action Potentials in a Peripheral Nerve By Brief Stimuli", Science magazine, vol. 206, Dec. 14, 1979, pp. 1311-1312.

Van Den Honert, et al. "A Technique for Collision Block of Peripheral Nerve: Frequency Dependence", IEEE Transactions of Biomedical Engineering, vol. BME-28, No. 5, May 1981, pp. 379-382.

Rijkhoff, N.J.M., et al. "Orderly recruitment of motoneurons in an acute rabbit model", 20th Annual International Conference of the IEEE Engineering in Medicine and Biology Society, vol. 20, No. 5, 1998, pp. 2564-2565.

Baratta, et al. "Orderly stimulation of Skeletal Muscle Motor Units with Tripolar Nerve Cuff Electrode", IEEE Transactions of Biomedical Engineering, vol. 36, No. 8, Aug. 1989, pp. 836-843.

Devor, M. "Pain Networks", Handbook of Brand Theory and Neural Networks, Ed. M.A. Arbib, MIT Press, p. 698, 1998.

U.S.Appl. No. 09-824,682 entitled "Method and Apparatus for Selective Control of Nerve Fibers" filed Apr. 4, 2001.

Cortese, J.F. "Vagus Nerve Stimulation for Control of Intractable Epileptic Seizures" available at http://www.acience.wayne.edu/~bio340/StudentPages/corese/, May 31, 2001.

Website: http://www.bcm/tmc.edu/neurol/struct/epilep/epilipsy_vagus.html, May 31, 2001.

Fitzpatrick, et al. "A Nerve Cuff Design for the Selective Activation and Blocking of Myelinated Nerve Fibres", Annual Conference of the IEEE Engineering in Medicine and Biology Society, vol. 13, No. 2, 1991.

Zhang, Y., et al., "Optimal Ventricular Rate Slowing During Atrial Fibrillation by Feedback AV Nodal-Selective Vagal Stimulation", Am. J. Physiol. Heart Circ. Physiol. 282:H1102-H1110.

Rijkoff, N.J.M., et al., "Selective Stimulation of Small Diameter Nerve Fibers in a Mixed Bundle", Proceedings of the Annual Project Meeting Sensations/Neuros and Mid Term Review Meeting Neuros, pp. 21-23, Apr. 1999.

Manfredi, M., "Differentiating Blocks of conduction of larger fibers in peripheral nerve by direct current", Arch. Ital. Biol., vol. 108, pp. 52-71, 1970.

* cited by examiner

NERVE STIMULATION FOR TREATING SPASTICITY, TREMOR, MUSCLE WEAKNESS, AND OTHER MOTOR DISORDERS

CROSS-REFERENCE TO RELATED APPLICATIONS

The present patent application is a continuation-in-part of U.S. patent application Ser. No. 09/843,334, filed Apr. 26, 2001, entitled, "Actuation and control of limbs through motor nerve stimulation."

The present patent application is a continuation of U.S. patent application Ser. No. 10/254,024 filed Sep. 24, 2002, now U.S. Pat. No. 6,892,098 which is a continuation-in-part of U.S. patent application Ser. No. 10/205,474 entitled, "Electrode assembly for nerve control," to Gross et al., filed Jul. 24, 2002, now U.S. No. Pat. 6,907,295 which is a continuation-in-part of PCT Patent Application PCT/IL02/00068, filed Jan. 23, 2002, entitled, "Treatment of disorders by unidirectional nerve stimulation," which is a continuation-in-part of U.S. patent application Ser. No. 09/944,913, filed Aug. 31, 2001, now U.S. Pat. No. 6,684,105 entitled, "Treatment of disorders by unidirectional nerve stimulation."

All of the above-cited patent applications are assigned to the assignee of the present patent application and are incorporated herein by reference.

FIELD OF THE INVENTION

The present invention relates generally to treating patients by application of electrical signals to a selected nerve or nerve bundle, and specifically to methods and apparatus for application of electrical signals to a selected nerve or nerve bundle for treating spasticity.

BACKGROUND OF THE INVENTION

Spasticity is characterized by continuous increased muscle tone (resistance), increased spinal reflexes, and involuntary muscle contractions. Spasticity causes muscle tightness, stiff, awkward movements, difficulty while moving, cramping, contractures (tendon shortening), and sometimes painful joints. Spasticity is often accompanied by muscle weakness.

There are a number of known causes of spasticity, tremors, and muscle weakness, including cerebral palsy, traumatic brain and spinal cord injury, stroke, multiple sclerosis, hereditary disorders, metabolic disorders, neurodegenerative diseases, irradiation of the brain and spinal cord, and tumors. Spasticity can also be of idiopathic origin.

Cerebral palsy (CP) is an upper motor neuron (UMN) disorder typically caused by brain injury at or around the time of birth, or in the first year of an infant's life. The most common type of CP is spastic CP, which causes spasticity, mainly of the flexor muscles of the arms and legs. In CP, spasticity is caused by cerebral lesions or UMN lesions in the spinal cord. An undamaged UMN inhibits the motor neurons that innervate skeletal muscles (alpha motor neurons) and the motor neurons that innervate muscle spindles of skeletal muscles (gamma motor neurons). Lesions decrease this inhibitory function of the UMN, resulting in over-activation of the alpha and gamma neurons, particularly in response to reflexes, resulting in spasticity.

FIG. 1 is a schematic illustration of example muscles and nerve fibers involved with spasticity, as is known in the art. FIG. 1 schematically illustrates the following nerve fibers:

(a) an afferent sensory fiber 40, such as a Ia sensory fiber, innervating a muscle spindle 50 of a muscle 14, such as a flexor muscle, (b) a gamma motor fiber 42 innervating muscle spindle 50, (c) an alpha motor fiber 44 innervating muscle 14, (d) a second alpha motor fiber 46 innervating a muscle 15 that is synergistic to muscle 14, and (e) a third alpha motor fiber 48 innervating a muscle 16, such as an extensor muscle, which is antagonistic to muscles 14 and 15.

All of these nerves terminate in a spinal cord 12 of the subject. Fibers 52 descend from an upper motor neuron (UMN) through spinal cord 12, and have an inhibiting effect on alpha motor fibers 44, 46 and 48, and gamma motor fiber 42.

During a stretch reflex, signals that muscle 14 is stretched are conveyed from muscle spindle 50 over sensory fiber 40 to spinal cord 12. These signals act by means of spinal cord circuitry to stimulate muscles 14 and 15 to contract, and indirectly on alpha motor fiber 48, by means of other spinal cord circuitry, which inhibits signals to antagonistic muscle 16, thereby causing it to relax. These actions combine to produce a coordinated reflex response. In addition, gamma motor fiber 42 "reloads" muscle spindle 50 during active contraction, thereby allowing the spindle to maintain its sensitivity over a wide range of muscle length.

FIG. 2 is a schematic illustration of the example muscles and some of the nerve fibers of FIG. 1, additionally including an example Ib sensory fiber 45, as is known in the art. When muscle 14 is stretched, a Golgi tendon organ 51 stimulates Ib sensory fiber 45. The Ib fiber acts (a) indirectly on alpha motor fibers 44 and 46, by means of spinal cord circuitry, which inhibit the motor neurons of these motor fibers and thereby relax muscles 14 and 15, and (b) indirectly on alpha motor fiber 48, by means of other spinal cord circuitry, which stimulates the motor fiber and thereby stimulates antagonistic muscle 16 to contract.

Current treatments for spasticity and/or CP include physical and occupational therapy, surgery, oral medications, and, more recently, chronic cerebellar stimulation and intrathecal baclofen (ITB) delivered by an implanted pump. Oral medication and physical therapy are generally the first-line treatment for spasticity and/or CP. Controversial treatments include electrical stimulation therapy.

Physical therapy is used to treat spasticity by exercising affected muscles in an attempt to keep joints movable and to preserve the range of motion and flexibility of muscles. Physical therapy for spasticity includes muscle stretching, range of movement exercises, functional retraining, bracing, and splinting. Occupational therapy is used to improve fine motor skills.

In the technique of chronic cerebellar stimulation (CCS), electrodes are implanted on the surface of the cerebellum and are used to stimulate certain cerebellar nerves. Davis R, in "Cerebellar stimulation for cerebral palsy spasticity, function, and seizures," Archives of Medical Research 31:290-299 (2000), which is incorporated herein by reference, reviews clinical studies of treatment by CCS. He reports that CCS reduced spasticity and athetoid movements in 85% of CP patients treated in eighteen clinics.

Electrical stimulation therapy is a controversial treatment for CP that is generally performed by using very low levels of electrical current to stimulate a desired muscle group to contract. The current is generally applied by electrodes placed on the skin. One type of electrical stimulation therapy, therapeutic electrical stimulation (TES), is administered at night during sleep.

Medications for treating spasticity and/or CP include oral medications such as benzodiazepines (e.g., diazepam and clonazepam), dantrolene, and, more recently, tizanidine (Zanaflex). Additionally, recent studies have shown that injecting Botox (the Botulinum toxin) into spastic muscles can bring relief by causing the muscles to relax.

Lesions decrease the inhibitory function of the UMN by preventing the UMN from sending signals that normally cause the release in the spinal cord of gamma aminobutyric acid (GABA), the most prevalent inhibitory neurotransmitter in the CNS. Baclofen is a medication with a chemical makeup almost identical to GABA. Administered baclofen can partially compensate for the deficiency of natural GABA, thereby treating spasticity. When baclofen is administered orally, a high dosage is necessary in order to achieve an effective concentration in the spinal cord.

PCT Patent Publication WO 01/10432 to Meythaler et al., which is incorporated herein by reference, describes a method for treating spastic disorders, convulsive disorders, pain and epilepsy by administering a therapeutically-effective amount of the compound gamma-aminobutyramide and analogs thereof.

Spasticity has recently been treated with Intrathecal Baclofen (ITB™) therapy, wherein baclofen is introduced directly into the central nervous system (CNS) by an implanted pump. Because baclofen is delivered directly into the spinal fluid, lower dosages are used than those used in oral therapy. Some patients have reported improvements in their conditions as a result of ITB therapy.

Surgery for treating CP includes orthopedic procedures to treat muscle contractures by releasing tendons, and rhizotomy. Rhizotomy is an invasive, irreversible procedure in which a neurosurgeon exposes nerves in the spinal canal that are going to and from muscles in the legs, and cuts about 30 to 50 percent of the dorsal half of each nerve. Spasticity in the legs is often permanently relieved, and, with intensive physical therapy, walking can often be improved. The procedure generally does not treat existing contractures. The procedure is generally considered appropriate only for four-to-seven-year-olds with good leg strength.

U.S. Pat. No. 6,356,784 to Lozano et al., which is incorporated herein by reference, describes techniques for treating movement disorders by stimulating the Pedunculopontine Nucleus (PPN), either electrically and/or by drug infusion. A sensor may be used to detect various symptoms of the movement disorders. A microprocessor algorithm may then analyze the output from the sensor to regulate the stimulation and/or drug therapy delivered to the PPN.

U.S. Pat. Nos. 5,832,932 and 5,711,316 to Elsberry et al., which are incorporated herein by reference, describe an implantable pump and catheter for infusing drugs into the brain to treat movement disorders resulting in abnormal motor behavior. A sensor may be used in combination with the implantable pump and catheter to generate a signal relating to the extent of the abnormal motor behavior. The therapeutic dosage may be regulated in response to the sensor signal so that the dosage is adjusted in response to an increase in the abnormal behavior, so as to decrease the abnormal motor behavior.

U.S. Pat. No. 6,094,598 to Elsberry et al., which is incorporated herein by reference, describes techniques that use one or more drugs and electrical stimulation to treat neural disorders, including movement disorders resulting in abnormal motor response, by means of an implantable signal generator and electrode and an implantable pump and catheter. A sensor is used to detect activity resulting from the neural disorder. A microprocessor algorithm analyzes the output from the sensor in order to regulate the stimulation and drug dosage delivered to the neural tissue.

U.S. Pat. No. 5,833,709 to Rise et al., which is incorporated herein by reference, describes techniques for stimulating the brain to treat movement disorders resulting in abnormal motor behavior by means of an implantable signal generator and electrode. A sensor is used to detect the symptoms resulting from the motion disorder. A microprocessor algorithm analyzes the output from the sensor in order to regulate the stimulation delivered to the brain.

U.S. Pat. No. 4,559,948 to Liss et al., which is incorporated herein by reference, describes cerebral palsy treatment apparatus employing a transcutaneously-applied electric signal to suppress pain and increase motor function. A first positive contact electrode is placed at the frontalis, and a second negative contact electrode is placed at the occiput of the head. Alternatively, the first positive contact electrode is placed at the cervical spinous process and the second negative contact electrode is placed at each affected muscle. An electric signal comprising relatively high frequency pulses with a low frequency amplitude modulation is then applied between the first and second electrodes.

U.S. Pat. No. 5,540,734 to Zabara, which is incorporated herein by reference, describes techniques for treating medical, psychiatric or neurological disorders by applying modulating electric signals to one or both of the trigeminal and glossopharyngeal nerves of a patient. The disorders described as being treatable, controllable or preventable by such nerve stimulation include motor disorders, Parkinson's disease, cerebral palsy, spasticity, chronic nervous illnesses and involuntary movement.

U.S. Pat. Nos. 5,178,161 and 5,314,495 to Kovacs, and U.S. Pat. No. 4,632,116 to Rosen, which are incorporated herein by reference, describe the use of microelectrodes to interface between control electronics and human nerves.

U.S. Pat. No. 4,649,936 to Ungar et al., which is incorporated herein by reference, describes an electrode cuff for placement around a nerve trunk, for generation of unidirectional propagating action potentials.

U.S. Pat. No. 5,199,430 to Fang et al., which is incorporated herein by reference, describes implantable electronic apparatus for assisting the urinary sphincter to relax.

U.S. Pat. No. 4,628,942 to Sweeney et al., which is incorporated herein by reference, describes an asymmetric, shielded, two-electrode cuff for stimulating a nerve.

U.S. Pat. No. 4,019,518 to Maurer et al., which is incorporated herein by reference, describes methods for using an electrical stimulation system to selectively stimulate portions of the body.

Many patents disclose other methods and devices for sensing muscular contractions and for applying muscular stimulation, including: U.S. Pat. No. 6,091,977 to Tarjan et al., U.S. Pat. No. 6,104,960 to Duysens et al., U.S. Pat. No. 6,086,525 to Davey et al., U.S. Pat. No. 4,926,865 to Oman, U.S. Pat. No. 4,392,496 to Stanton, and U.S. Pat. No. 6,146,335 to Gozani, which are incorporated herein by reference.

U.S. Pat. No. 6,119,516 to Hock, which is incorporated herein by reference, describes a biofeedback system, optionally including a piezoelectric element, which measures the motions of joints in the body.

U.S. Pat. No. 5,069,680 to Grandjean, which is incorporated herein by reference, describes the use of a piezoelectric crystal as a muscle activity sensor.

A number of techniques are known for inhibiting or stimulating motor nerves controlling muscular or glandular activities. These include collision blocking, high frequency blocking, and anodal blocking.

In collision blocking, a unidirectional action potential is induced by external electrodes to travel towards the muscle or gland being controlled. These electrode-generated action potentials collide with, and thereby block, the body-generated action potentials.

U.S. Patent Application Publication 2002-0099419 corresponding to U.S. patent application Ser. No. 09/824,682 to Cohen and Ayal, and PCT Patent Publication 02/58782 to Cohen and Ayal, both entitled, "Method and apparatus for selective control of nerve fibers," and assigned to the assignee of the present patent application and incorporated herein by reference, describe a method particularly useful for pain control. The propagation of body-generated action potentials traveling through a nerve bundle is selectively blocked by using a tripolar electrode device to generate unidirectional action potentials which block, by collision blocking, the body-generated action potentials representing pain sensations in the small-diameter sensory fibers. In the described preferred embodiments, a plurality of electrode devices spaced along the length of the nerve bundle are sequentially actuated with inter-device delays corresponding to the velocity of propagation of the body-generated action potentials through the large-diameter fibers to produce an effect analogous to a wave of green traffic lights, which minimizes undesired anodal blocking of the large-diameter fibers while maximizing the collision blocking of the small-diameter fibers.

In high frequency blocking, high frequency (e.g., 600 Hz) stimulations are used to block the transmission of action potentials through the blocked nerve fibers.

In anodal blocking, nerve fibers are locally hyperpolarized by anodal current. If sufficiently hyperpolarized, action potentials are not able to propagate through the hyperpolarized zone and are blocked.

The anodal block has been investigated for producing selective blocking of the action potentials through selected motor nerve fibers, particularly the larger-diameter nerve fibers which are more sensitive to the hyperpolarization. Unblocked electrode-generated action potentials (or those blocked to a lesser degree) passing through the anodal block generate collision blocks. These collision blocks enable the selective control of motor nerve fibers in order to stimulate or suppress, as the case may be, selected muscular or glandular activities. See, for example, van den Honert C et al., "A technique for collision blocks of peripheral nerve: single stimulus analysis," IEEE Transactions on Biomedical Engineering, 28(5), 373-378 (1981), which is incorporated herein by reference.

A number of patents and articles describe methods and devices for stimulating nerves to achieve a desired effect. Often these techniques include a design for an electrode or electrode cuff.

U.S. Pat. No. 4,608,985 to Crish et al., which is incorporated herein by reference, describes electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Agnew W F et al., "Microstimulation of the lumbosacral spinal cord," Huntington Medical Research Institutes Neurological Research Laboratory, Sep. 30, 1995-Sep. 29, 1998.

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20 (5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989).

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

SUMMARY OF THE INVENTION

It is an object of some aspects of the present invention to provide improved apparatus and methods for treating and controlling spasticity and/or tremors caused by motor disorders, such as cerebral palsy (CP).

It is also an object of some aspects of the present invention to provide improved apparatus and methods for treating muscle weakness caused motor disorders.

It is a further object of some aspects of the present invention to provide improved apparatus and methods for treating and controlling spasticity by application of electrical signals to selected nerves or nerve fibers in the body of a subject.

It is yet a further object of some aspects of the present invention to provide apparatus and methods treating and controlling spasticity and/or tremors without the systemic side effects sometimes caused by pharmaceutical treatments of spasticity.

It is an additional object of some aspects of the present invention to provide apparatus and methods treating muscle weakness without the systemic side effects sometimes caused by pharmaceutical treatments of muscle weakness.

In preferred embodiments of the present invention, apparatus for treating a movement disorder such as spasticity or tremor of a subject comprises (a) an electrode device that is applied to a nerve that directly or indirectly innervates a skeletal muscle of the subject, and (b) a control unit, coupled to the electrode device, which causes a current to pass through the electrode device into the nerve. The control unit drives the current in order to inhibit or stimulate one or more nerve fibers in the nerve, so as to inhibit a reflex arc causing excessive contraction of the skeletal muscle. The treatment is applied to a flexor muscle or an extensor muscle, or, for some applications, to extensor and flexor muscles of an extensor/flexor muscle pair.

In some preferred embodiments of the present invention, the electrode device is applied to a nerve that includes at least one sensory nerve fiber, such as a Ia sensory fiber that innervates a muscle spindle of a skeletal muscle of the subject. The control unit drives the electrode device to apply a current that inhibits the propagation of afferent action potentials traveling in the sensory fiber from the muscle spindle to the spinal cord. When not properly inhibited, these action potentials provide an indication that the muscle is undesirably extended and therefore in need of compensating contractions to provide stability. These action potentials indirectly stimulate the muscle and synergistic muscles to contract (autogenetic excitation), and induce antagonistic muscles to relax. By inhibiting these action potentials, the application of the current as described herein compensates, at least partially, for the reduced inhibition applied to the reflex arc due to the damaged UMN or due to other causes. As a result, spasticity of the extensor/flexor muscle pair is typically reduced.

Alternatively or additionally, the electrode device is applied to a nerve that includes at least one sensory nerve fiber, such as a Ib sensory fiber that innervates a Golgi tendon organ of a skeletal muscle of the subject. The control unit drives the electrode device to apply a current that stimulates the propagation of afferent action potentials in the sensory fiber from the Golgi tendon organ to the spinal cord. These action potentials indirectly stimulate the antagonistic muscle to contract and induce synergistic muscles to relax. By inducing these action potentials, the application of the current compensates, at least partially, for the reduced inhibition applied to the reflex arc due to the damaged UMN or due to other causes. As a result, such stimulation achieves an effect generally similar to (and often complementary with) that achieved by inhibition of Ia sensory fibers, thereby typically reducing spasticity of the extensor/flexor muscle pair.

Further alternatively or additionally, the electrode device is applied to a nerve that includes at least one gamma motor fiber that innervates a muscle spindle of a skeletal muscle. In this case, the control unit drives the electrode device to apply a current that inhibits efferent action potentials traveling in the gamma motor fiber from the spinal cord to the muscle spindle. When not inhibited, gamma motor fibers contract the muscle spindle during active contraction, thereby allowing the spindle to maintain its sensitivity over a wide range of muscle length. Inhibition of these gamma motor fiber action potentials reduces the sensitivity of the muscle spindles, resulting in reduced activation of Ia sensory fibers. As a result, such gamma motor fiber inhibition achieves an effect generally similar to that achieved by direct inhibition of Ia sensory fibers.

Still further alternatively or additionally, the electrode device is applied to a nerve that includes at least one alpha motor fiber. In this case, the control unit drives the electrode device to apply a current that inhibits efferent action potentials traveling in the alpha motor fiber from the spinal cord to the skeletal muscle. As a result, the limb is partially paralyzed, which typically reduces spasticity.

In some preferred embodiments of the present invention, muscle weakness is treated by:
  (a) inhibiting propagation of afferent action potentials in one or more sensory fibers, preferably Ia sensory fibers, that innervate a skeletal muscle, and/or (b) inhibiting propagation of efferent action potentials in one or more gamma motor fibers that innervate a skeletal muscle; and
  (a) stimulating one or more non-gamma motor fibers that innervate the muscle, and/or (b) directly stimulating the muscle, as opposed to a nerve that innervates the muscle.

As a result of the muscle stimulation, muscle strength, which is frequently reduced by spasticity, is generally at least partially restored. At the same time, inhibition of the sensory fiber or the gamma motor fiber moderates the reflex arc, thereby reducing spasticity, as described above.

In some preferred embodiments of the present invention, spasticity is treated by applying an electrode device to a nerve in the spinal cord, and the control unit drives the electrode device to apply a current so as to stimulate a subset of fibers of the nerve that include one or more fibers descending from a UMN. This stimulation generates efferent action potentials in the UMN fibers. These action potentials typically have generally the same effect as action potentials propagated naturally in undamaged UMN fibers, which is to inhibit alpha motor neurons that innervate skeletal muscles. As a result, the exaggerated reflex arc associated with spasticity is generally at least partially inhibited.

For the embodiments described hereinabove, the control unit preferably comprises circuitry and/or software which regulates the magnitude, frequency, and/or duration of the electric field generated by individual electrodes within the electrode devices. This regulation is preferably performed in real time by utilizing a function, the inputs of which include one or more constants and/or physiological parameters measured in real time. Optionally, the constants are pre-set for a given condition. The physiological parameters are preferably indicative of the onset or strength of spastic muscle contraction and/or limb movement. The control unit preferably comprises a sensor unit for measuring the physiological parameters. For some applications, techniques for measuring muscle activity or limb motion described in references cited in the Background section of the present patent application are adapted for use with these embodiments of the present invention.

Advantageously, the techniques described herein generally cause the treated nerves to mimic their natural function in the absence of the disorder causing spasticity.

Spasticity, tremor and/or muscle weakness caused by many diseases of or injuries to the central nervous system are amenable to treatment by the techniques described herein. For example, cerebral palsy, traumatic brain and spinal cord injury, stroke, multiple sclerosis, hereditary disorders, metabolic disorders, neurodegenerative diseases, irradiation of the brain and spinal cord, and tumors, often cause spasticity, tremors, and/or muscle weakness. Spasticity of idiopathic origin and essential tremor are also amendable to treatment with the techniques described herein. It is noted that although some preferred embodiments of the present invention are described herein with respect to treating spasticity, this is by way of illustration and not limitation, and the scope of the present invention includes applying some or all of the techniques described herein in the treatment of other movement disorders, such as tremor and muscle weakness.

There is therefore provided, in accordance with a preferred embodiment of the present invention, a method for treating spasticity of a subject, including:

driving a current into a nerve of the subject that includes one or more sensory fibers; and configuring the current so as to inhibit propagation of action potentials in one or more of the sensory fibers, so as to treat the spasticity.

In a preferred embodiment, the sensory fibers include one or more Ia sensory fibers, and configuring the current includes configuring the current so as to inhibit propagation of the action potentials in at least one of the Ia sensory fibers.

In a preferred embodiment, the nerve includes a nerve selected from the list consisting of: a tibial nerve, a sciatic nerve, a femoral nerve, a median nerve, a musculocutaneous nerve, an ulnar nerve, and a radial nerve, and wherein driving the current includes driving the current into the nerve.

For some applications, the method includes implanting a device in a body of the subject, wherein driving the current includes driving the current at the device.

In an embodiment of the present invention, driving the current includes driving the current at a site in a limb of the subject. Alternatively or additionally, driving the current includes driving the current in a vicinity of a spinal cord nerve root of the subject. For some applications, driving the current includes driving the current in a series of pulses.

In a preferred embodiment, configuring the current includes configuring the current to have a frequency greater than about 5 Hz, so as to inhibit propagation of the action potentials.

For some applications, the method includes determining a time of day, wherein driving the current includes driving the current responsive to the time of day.

In a preferred embodiment, driving the current includes driving the current into a portion of the nerve proximal to a spinal cord of the subject. For example, driving the current into the portion of the nerve proximal to the spinal cord of the subject may include driving the current into the portion of the nerve at a site within about 5 cm from the spinal cord.

In a preferred embodiment, configuring the current includes configuring the current to apply collision blocking to the nerve so as to inhibit propagation of the action potentials. For example, driving the current may include sequentially driving the current at a plurality of locations on the nerve with delays timed responsive to a velocity of propagation of body-generated action potentials traveling in the nerve, so as to inhibit propagation of the action potentials while minimizing inhibition of propagation of the body-generated action potentials.

In a preferred embodiment, the current includes a first current, the nerve includes a first nerve that includes one or more first sensory fibers, configuring the current includes configuring the first current so as to inhibit propagation of first action potentials in one or more of the first sensory fibers, and the method includes driving a second current into a second nerve of the subject that innervates a second muscle of the subject that is antagonistic to a first muscle innervated by at least one of the first sensory fibers, the second nerve including one or more second sensory fibers. In this case, the method also typically includes configuring the second current so as to inhibit propagation of second action potentials in at least one of the second sensory fibers. For some applications, the first nerve includes the second nerve (i.e., may be identical to the second nerve), and driving the second current includes driving the second current into the first nerve. Alternatively, the first and second nerves include two distinct nerves of the subject.

In a preferred embodiment, the current includes a first current, the nerve includes a first nerve that includes one or more first sensory fibers, configuring the current includes configuring the first current so as to inhibit propagation of first action potentials in one or more of the first sensory fibers, and the method includes (a) driving a second current into a second nerve of the subject that innervates a second muscle of the subject that is synergistic to a first muscle innervated by at least one of the first sensory fibers, the second nerve including one or more second sensory fibers, and (b) configuring the second current so as to inhibit propagation of second action potentials in at least one of the second sensory fibers. For some applications, the first nerve includes the second nerve, and driving the second current includes driving the second current into the first nerve. Alternatively, the first and second nerves include two distinct nerves of the subject.

In a preferred embodiment, the current includes a first current, the nerve includes a first nerve that includes one or more first sensory fibers, configuring the current includes configuring the first current so as to inhibit propagation of first action potentials in one or more of the first sensory fibers, and the method includes:

driving a second current into a second nerve of the subject that includes one or more gamma motor fibers innervating a muscle spindle of the subject; and configuring the second current so as to inhibit propagation of second action potentials in at least one of the gamma motor fibers.

For some applications, the first nerve includes the second nerve, and driving the second current includes driving the second current into the first nerve. Alternatively, the first and second nerves include two distinct nerves of the subject.

In a preferred embodiment, the method includes sensing at least one physiological parameter of the subject, wherein driving the current includes driving the current responsive to the at least one physiological parameter. For example, the at least one physiological parameter may include a measure selected from the list consisting of:
a measure of electrical activity of one or more muscles of the subject,
a measure of mechanical strain of one or more muscles of the subject,
a measure of motion of one or more limbs of the subject,
a measure indicating that the subject is sleeping, and
a measure of an action potential in one or more nerve fibers of the subject,
wherein driving the current includes driving the current responsive to the at least one physiological parameter.

For some applications, the method includes analyzing the at least one physiological parameter to determine a measure of spasticity of the subject, wherein driving the current includes driving the current responsive to the measure of spasticity so as to reduce the measure of spasticity.

There is also provided, in accordance with a preferred embodiment of the present invention, a method for treating spasticity of a subject, including:

driving a current into a nerve of the subject that includes one or more sensory fibers; and configuring the current so as to induce propagation of action potentials in one or more of the sensory fibers, so as to treat the spasticity.

In a preferred embodiment, the sensory fibers include one or more Ib sensory fibers, and wherein configuring the current includes configuring the current so as to induce propagation of the action potentials in at least one of the Ib sensory fibers.

In a preferred embodiment, the current includes a first current, the nerve includes a first nerve that includes one or more first sensory fibers, configuring the current includes configuring the first current so as to induce propagation of first action potentials in one or more of the first sensory fibers, and the method includes:

driving a second current into a second nerve of the subject that includes one or more second sensory fibers; and configuring the second current so as to inhibit propagation of second action potentials in one or more of the second sensory fibers.

For some applications, the second sensory fibers include one or more Ia sensory fibers, and configuring the second current includes configuring the second current so as to inhibit propagation of the second action potentials in at least one of the Ia sensory fibers.

There is further provided, in accordance with a preferred embodiment of the present invention, a method for treating spasticity of a subject, including:

driving a current into a nerve of the subject that includes one or more gamma motor fibers innervating a muscle spindle of a muscle of the subject; and configuring the current so as to inhibit propagation of action potentials in at least one of the gamma motor fibers, so as to treat the spasticity.

In a preferred embodiment, the current includes a first current, the nerve includes a first nerve that includes the one or more gamma motor fibers innervating the muscle spindle of the muscle of the subject, configuring the current includes configuring the first current so as to inhibit propagation of first action potentials in at least one of the gamma motor fibers, and the method includes:

driving a second current into a second nerve of the subject that includes one or more sensory fibers; and configuring the second current so as to inhibit propagation of second action potentials in one or more of the sensory fibers.

In a preferred embodiment, the sensory fibers include one or more Ia sensory fibers, and wherein configuring the second current includes configuring the second current so as to inhibit propagation of the second action potentials in at least one of the Ia sensory fibers.

There is still further provided, in accordance with a preferred embodiment of the present invention, a method for treating a weakness of a skeletal muscle of a subject, including:

driving an inhibiting current into a first nerve of the subject that includes one or more sensory fibers innervating the muscle, so as to inhibit propagation of afferent action potentials in the sensory fibers; and driving a stimulating current into a second nerve of the subject that includes one or more motor fibers innervating the muscle, so as to stimulate efferent action potentials in the motor fibers.

In a preferred embodiment, the sensory fibers include one or more Ia sensory fibers, and driving the inhibiting current includes driving the inhibiting current so as to inhibit propagation of action potentials in at least one of the Ia sensory fibers. Alternatively or additionally, the motor fibers include one or more alpha motor fibers, and driving the stimulating current includes driving the stimulating current so as to stimulate efferent action potentials in at least one of the alpha motor fibers. Still further alternatively or additionally, the motor fibers include one or more A-beta motor fibers, and driving the stimulating current includes driving the stimulating current so as to stimulate efferent action potentials in at least one of the A-beta motor fibers.

For some applications, the second nerve includes a set of nerve fibers, and wherein driving the stimulating current into the second nerve includes applying to the second nerve a secondary inhibiting current which is capable of inhibiting efferent action potentials in the set of nerve fibers that are induced by the stimulating current, the nerve fibers in the set having generally larger diameters than the motor fibers.

In a preferred embodiment, driving the stimulating current into the second nerve includes applying to the second nerve a supplementary inhibiting current, which is configured to inhibit action potentials traveling in an afferent direction in one or more nerve fibers in the second nerve that are induced by the stimulating current.

There is yet further provided, in accordance with a preferred embodiment of the present invention, a method for treating spasticity of a subject, including:

driving a current into a nerve of the subject that includes one or more motor fibers; and configuring the current so as to inhibit propagation of efferent action potentials in one or more of the motor fibers, so as to treat the spasticity.

In a preferred embodiment of the present invention, the motor fibers include one or more alpha motor fibers, and wherein configuring the current includes configuring the current so as to inhibit propagation of efferent action potentials in the alpha motor fibers.

There is also provided, in accordance with a preferred embodiment of the present invention, a method for treating a weakness of a skeletal muscle of a subject, including:

driving an inhibiting current into a first nerve of the subject that includes one or more gamma motor fibers innervating the muscle, so as to inhibit propagation of efferent action potentials in the gamma motor fibers; and driving a stimulating current into a second nerve of the subject that includes one or more motor fibers innervating the muscle, so as to stimulate efferent action potentials in the motor fibers.

For some applications, the motor fibers include one or more alpha motor fibers, and driving the stimulating current includes driving the stimulating current so as to stimulate efferent action potentials in the alpha motor fibers. Alternatively or additionally, the motor fibers include one or more A-beta motor fibers, and driving the stimulating current includes driving the stimulating current so as to stimulate efferent action potentials in the A-beta motor fibers.

There is additionally provided, in accordance with a preferred embodiment of the present invention, a method for treating a weakness of a skeletal muscle of a subject, including:

driving an inhibiting current into a nerve of the subject that includes one or more sensory fibers innervating the muscle, so as to inhibit propagation of afferent action potentials in the sensory fibers; and driving a stimulating current into the muscle, so as to stimulate the muscle.

There is yet additionally provided, in accordance with a preferred embodiment of the present invention, a method for treating a weakness of a skeletal muscle of a subject, including:

driving an inhibiting current into a nerve of the subject that includes one or more gamma motor fibers innervating the muscle, so as to inhibit propagation of efferent action potentials in the gamma motor fibers; and driving a stimulating current into the muscle, so as to stimulate the muscle.

There is still additionally provided, in accordance with a preferred embodiment of the present invention, a method for treating spasticity of a subject, including:

driving a current into a spinal cord of the subject; and configuring the current so as to stimulate a subset of fibers of the spinal cord that include one or more fibers descending from an upper motor neuron (UMN), so as to treat the spasticity.

For some applications, driving the current includes driving the current into a nerve tract of the spinal cord, which nerve tract includes the subset of fibers. Alternatively or additionally, driving the current includes driving the current onto a surface of the spinal cord.

In a preferred embodiment, the current includes a first current, configuring the current includes configuring the first current so as to stimulate the subset of fibers of the spinal cord, and the method includes:

driving a second current into a nerve of the subject that includes one or more gamma motor fibers innervating a muscle spindle of the subject; and configuring the second current so as to inhibit propagation of action potentials in at least one of the gamma motor fibers.

In a preferred embodiment, the current includes a first current, configuring the current includes configuring the first current so as to stimulate the subset of fibers of the spinal cord, and the method includes:

driving a second current into a nerve of the subject that includes one or more sensory fibers; and configuring the second current so as to inhibit propagation of action potentials in one or more of the sensory fibers.

For some applications, the sensory fibers include one or more Ia sensory fibers, and wherein configuring the second current includes configuring the second current so as to inhibit propagation of the action potentials in at least one of the Ia sensory fibers.

There is further provided, in accordance with a preferred embodiment of the present invention, apparatus for treating spasticity of a subject, including:

an electrode device, adapted to be coupled to a nerve of the subject that includes one or more sensory fibers; and a control unit, adapted to drive the electrode device to apply to the nerve a current that is capable of inhibiting propagation of action potentials in at least one of the sensory fibers, so as to treat the spasticity.

In a preferred embodiment, the electrode device includes:

a cathode, adapted to apply to the nerve a stimulating current that is capable of inducing action potentials in the nerve;

a first set of one or more anodes, adapted to be disposed on one side of the cathode, and to apply to the nerve a first inhibiting current that is capable of inhibiting action potentials in the nerve so as to produce a selective anodal block of the nerve; and a second set of one or more anodes, adapted to be disposed on a second side of the cathode opposite the first set of anodes, and to apply to the nerve a second inhibiting current which is capable of inhibiting action potentials in the nerve so as to produce an essentially complete anodal block of the nerve.

In a preferred embodiment, the apparatus includes a sensor unit, and the control unit is adapted to receive at least one sensed parameter from the sensor unit, and to drive the electrode device to apply the current responsive to the at least one sensed parameter. For some applications, the sensor unit includes an electromyographic (EMG) monitor, the at least one sensed parameter includes a measure of electrical activity of one or more muscles of the subject, and the control unit is adapted to receive the at least one sensed parameter from the EMG monitor.

Alternatively or additionally, the sensor unit includes a strain gauge, the at least one sensed parameter includes a measure of mechanical strain of one or more muscles of the subject, and the control unit is adapted to receive the at least one sensed parameter from the strain gauge. Further alternatively or additionally, the sensor unit includes an accelerometer, the at least one sensed parameter includes a measure of motion of one or more limbs of the subject, and the control unit is adapted to receive the at least one sensed parameter from the accelerometer.

There is yet further provided, in accordance with a preferred embodiment of the present invention, apparatus for treating spasticity of a subject, including:

an electrode device, adapted to be coupled to a nerve of the subject that includes one or more sensory fibers; and a control unit, adapted to drive the electrode device to apply to the nerve a current that is capable of inducing propagation of action potentials in at least one of the sensory fibers, so as to treat the spasticity.

There is still further provided, in accordance with a preferred embodiment of the present invention, apparatus for treating spasticity of a subject, including:

an electrode device, adapted to be coupled to a nerve of the subject that includes one or more gamma motor fibers innervating a muscle spindle of a muscle of the subject; and a control unit, adapted to drive the electrode device to apply to the nerve a current that is capable of inhibiting propagation of action potentials in at least one of the gamma motor fibers, so as to treat the spasticity.

There is also provided, in accordance with a preferred embodiment of the present invention, apparatus for treating a weakness of a skeletal muscle of a subject, including:

a first electrode device, adapted to be coupled to a first nerve of the subject that includes one or more sensory fibers innervating the muscle;

a second electrode device, adapted to be coupled to a second nerve of the subject that includes one or more motor fibers innervating the muscle; and a control unit, adapted to:

drive the first electrode device to apply to the first nerve an inhibiting current, which is capable of inhibiting propagation of afferent action potentials in the sensory fibers, and drive the second electrode device to apply to the second nerve a stimulating current, which is capable of stimulating efferent action potentials in the motor fibers.

There is additionally provided, in accordance with a preferred embodiment of the present invention, apparatus for treating spasticity of a subject, including:

an electrode device, adapted to be coupled to a nerve of the subject that includes one or more motor fibers; and a control unit, adapted to drive the electrode device to apply to the nerve a current, which is capable of inhibiting propagation of efferent action potentials in one or more of the motor fibers, so as to treat the spasticity.

There is yet additionally provided, in accordance with a preferred embodiment of the present invention, apparatus for treating a weakness of a skeletal muscle of a subject, including:

a first electrode device, adapted to be coupled to a first nerve of the subject that includes one or more gamma motor fibers innervating the muscle;

a second electrode device, adapted to be coupled to a second nerve of the subject that includes one or more motor fibers innervating the muscle; and a control unit, adapted to:

drive the first electrode device to apply to the first nerve an inhibiting current, which is capable of inhibiting propagation of efferent action potentials in the gamma motor fibers, and drive the second electrode device to apply to the second nerve a stimulating current, which is capable of stimulating efferent action potentials in the motor fibers.

There is still additionally provided, in accordance with a preferred embodiment of the present invention, apparatus for treating a weakness of a skeletal muscle of a subject, including:

a first electrode device, adapted to be coupled to a nerve of the subject that includes one or more sensory fibers innervating the muscle;

a second electrode device, adapted to be coupled to the muscle; and a control unit, adapted to:

drive the first electrode device to apply to the nerve an inhibiting current, which is capable of inhibiting propagation of afferent action potentials in the sensory fibers, and drive the second electrode device to apply a stimulating current to the muscle.

There is also provided, in accordance with a preferred embodiment of the present invention, apparatus for treating a weakness of a skeletal muscle of a subject, including:

a first electrode device, adapted to be coupled to a nerve of the subject that includes one or more gamma motor fibers innervating the muscle;

a second electrode device, adapted to be coupled to the muscle; and a control unit, adapted to:

drive the first electrode device to apply to the nerve an inhibiting current, which is capable of inhibiting propagation of efferent action potentials in the gamma motor fibers, and drive the second electrode device to apply a stimulating current to the muscle.

There is further provided, in accordance with a preferred embodiment of the present invention, apparatus for treating spasticity of a subject, including:

an electrode device, adapted to be coupled to a spinal cord of the subject; and a control unit, adapted to drive the electrode device to apply to the spinal cord a current, which is capable of stimulating a subset of fibers of the spinal cord that includes one or more fibers descending from an upper motor neuron (UMN), so as to treat the spasticity.

The present invention will be more fully understood from the following detailed description of a preferred embodiment thereof, taken together with the drawings, in which:

DETAILED DESCRIPTION OF PREFERRED EMBODIMENTS

Figure 1:
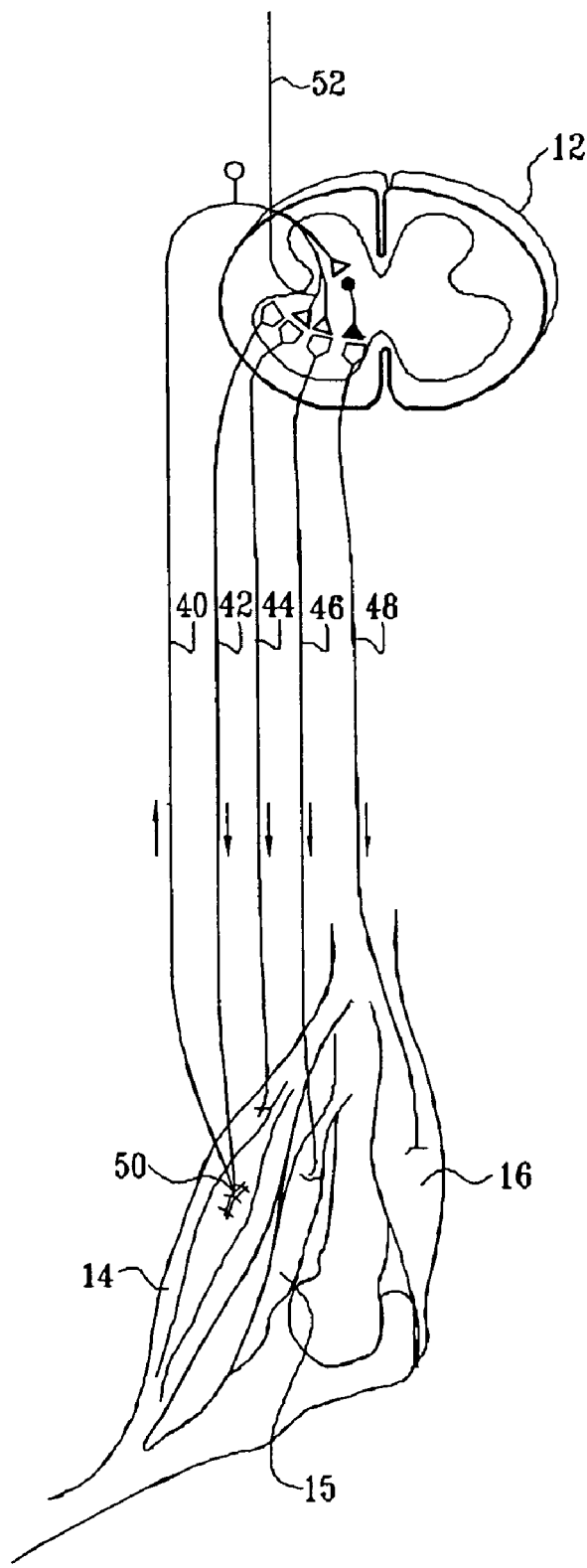
FIG. 1 is a schematic illustration of example muscles and nerve fibers involved with spasticity, as is known in the prior art.
Figure 2:
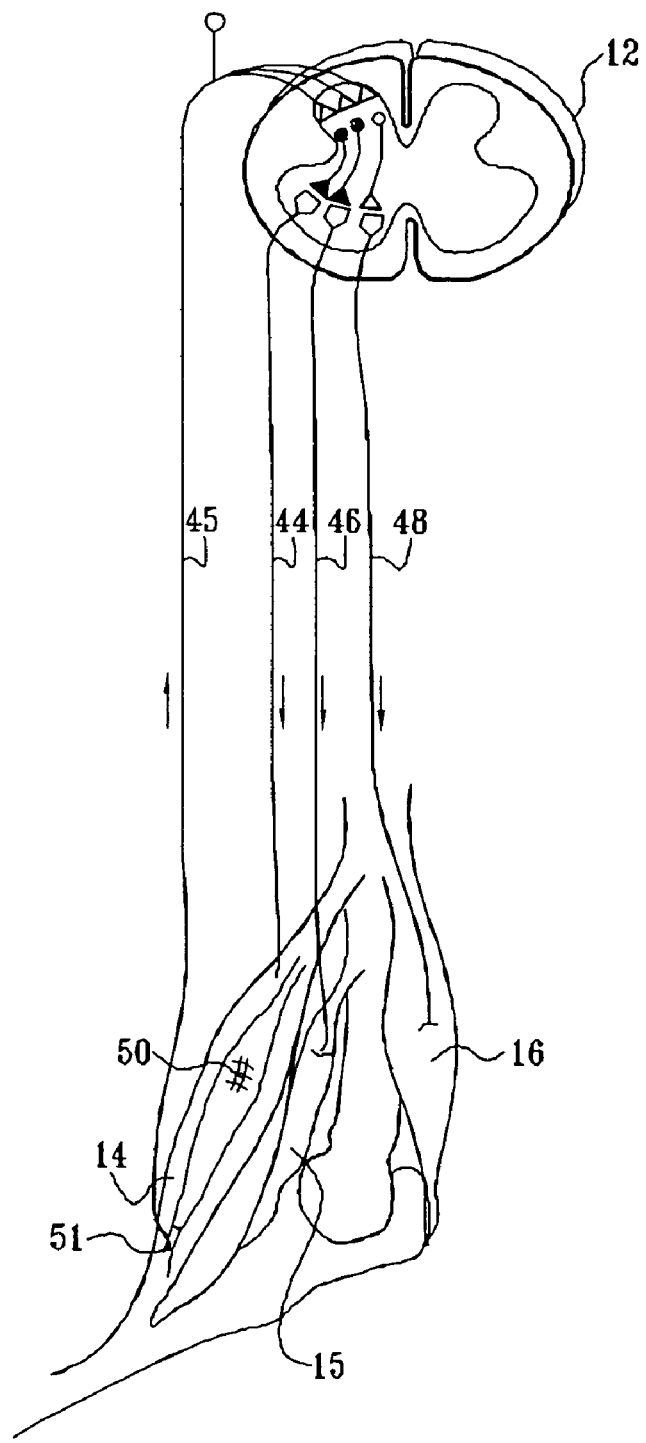
FIG. 2 is a schematic illustration of the example muscles and some of the nerve fibers of FIG. 1, additionally including an example Ib sensory fiber, as is known in the prior art.
Figure 3:
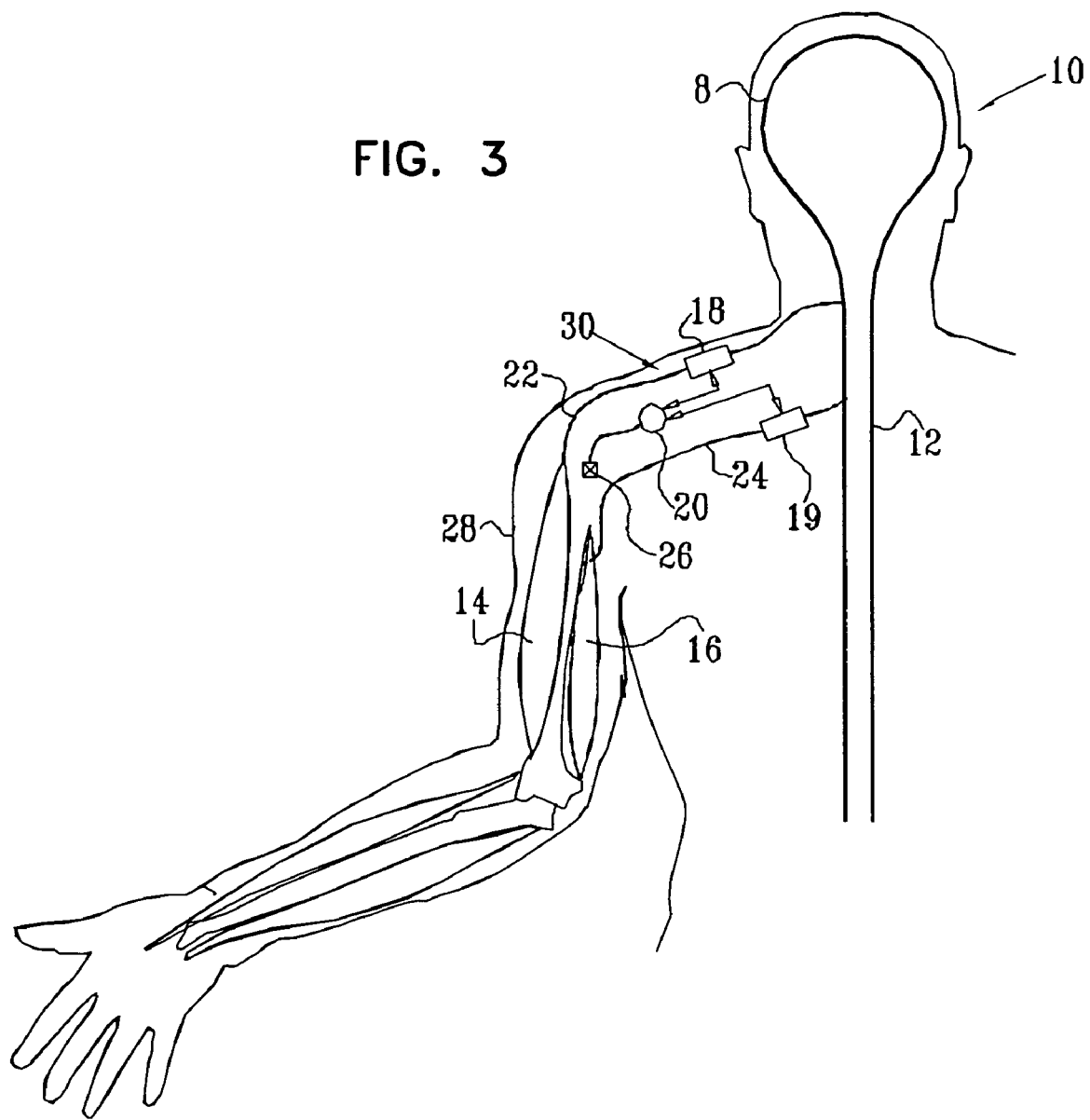
FIG. 3 is a schematic illustration of a spasticity treatment system applied to a subject, in accordance with a preferred embodiment of the present invention.

FIG. 3 is a schematic illustration of a spasticity treatment system 30 comprising an electrode device 18, in accordance with a preferred embodiment of the present invention. Electrode device 18 is applied to a nerve 22 that directly or indirectly innervates a skeletal muscle 14 of a subject 10. Typically, system 30 is utilized for treating spasticity and/or muscle weakness caused by a motor disorder such as cerebral palsy (CP). System 30 further comprises an implanted or external control unit 20, coupled to electrode device 18. Control unit 20 drives electrode device 18 to apply signals to inhibit or stimulate one or more nerve fibers of nerve 22, so as to inhibit a reflex arc, such as a stretch reflex arc, in a limb 28 of subject 10, which reflex arc is causing excessive contraction of a skeletal muscle 14, its synergistic muscles, such as muscle 15, and its antagonistic muscles, such as muscle 16.

System 30 optionally comprises one or more additional electrode devices, such as an electrode device 19, which is substantially similar to electrode device 18, applied to a nerve 24 that innervates a muscle 16 that is antagonistic to muscle 14. As appropriate for treating spasticity, control unit 20 drives electrode device 18, electrode device 19, or both electrode devices to apply signals to inhibit or stimulate one or more nerve fibers. For some applications, electrode devices 18 and 19 share at least one electrode in common. Preferably, system 30 further comprises at least one sensor unit 26, as described below.

FIG. 3 shows system 30 applied to skeletal muscles of an arm by way of example only. System 30 can be applied to other skeletal muscles of subject 10, such as skeletal muscles of the hand, leg, and foot. Likewise, although muscles 14 and 16 are shown as biceps brachii and triceps brachii, respectively, this is by way of example only. Furthermore, although nerves 22 and 24 are shown as the musculocutaneous nerve and the radial nerve, respectively, this also is by way of example only, and other nerves of the body can be stimulated or inhibited using the techniques described herein, including the tibial nerve, the sciatic nerve, the ulnar nerve, the femoral nerve, and the median nerve.

Figure 4:
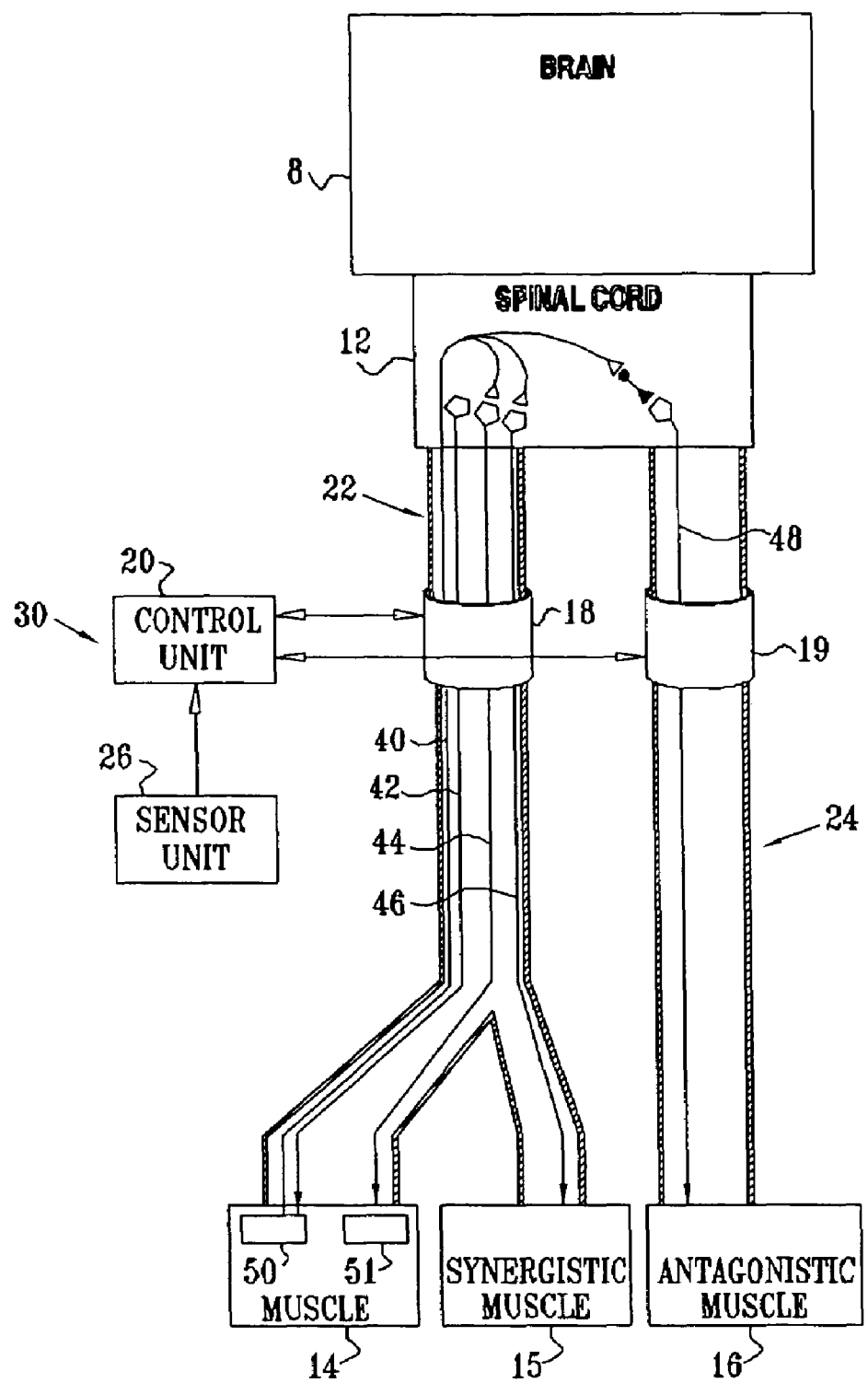
FIG. 4 is a block diagram that schematically illustrates the spasticity treatment system of FIG. 3 applied to nerves of a subject, in accordance with a preferred embodiment of the present invention.

FIG. 4 is a block diagram that schematically illustrates system 30 applied to nerve 22 that innervates a muscle 14 of subject 10, and, optionally, a second muscle 15 that is synergistic to muscle 14, in accordance with a preferred embodiment of the present invention. Muscles 14 and 15 are typically either flexor muscles (as shown in FIG. 3) or extensor muscles. Nerve 22 is shown as including (a) at least one sensory fiber 40, such as a Ia sensory fiber, innervating a muscle spindle 50 of muscle 14, (b) at least one gamma motor fiber 42, also innervating muscle spindle 50, and (c) at least one alpha motor fiber 44 and at least one alpha motor fiber 46 innervating muscle 14 and synergistic muscle 15, respectively.

Although system 30 for simplicity is shown and described as being configured to apply current to sensory and motor fibers of muscle 14 only, for some applications the system is additionally configured to apply current to sensory and/or motor fibers of one or more synergistic muscles, such as synergistic muscle 15. Furthermore, for some applications, system 30 is additionally configured to apply current to sensory and/or motor fibers of one or more antagonistic muscles, such as antagonistic muscle 16. Although the fibers leading to muscle 14 and synergistic muscle 15, on the one hand, and to antagonistic muscle 16, on the other hand, are shown in FIG. 4 as contained in separate nerves, some or all of these fibers are sometimes contained within a single nerve bundle, or in separate nerve bundles within a single nerve.

In a preferred embodiment of the present invention, control unit 20 drives electrode device 18 to apply a current that inhibits the propagation of afferent action potentials traveling from muscle spindle 50 to spinal cord 12 in sensory fiber 40, which preferably includes a Ia sensory fiber. When not properly inhibited, these action potentials provide an incorrect indication to spinal cord 12 that muscle 14 is undesirably extended and therefore in need of compensating contractions to provide stability. The action potentials providing the incorrect indication may directly stimulate muscle 14 and synergistic muscles 15 to contract (autogenetic excitation), and indirectly induce antagonistic muscle 16 to relax. By inhibiting the action potentials that provide the incorrect indication, as described herein, the application of the current compensates, at least partially, for the reduced inhibition applied to the reflex arc due to the damaged UMN or due to other causes. As a result of the inhibition induced by control unit 20, spasticity of the extensor/flexor muscle pair is typically reduced. In this embodiment, electrode device 18 preferably is applied to nerve 22 in the vicinity of spinal cord 12, e.g., at or near a nerve root, or, alternatively, at a site on a peripheral nerve, such as at a site in a limb of the subject.

In a preferred embodiment of the present invention, control unit 20 drives electrode device 18 to apply a current that inhibits efferent action potentials traveling in gamma motor fiber 42 from spinal cord 12 to muscle spindle 50 of muscle 14. When not inhibited, gamma motor fibers contract the muscle spindle during active contraction, thereby allowing the spindle to maintain its sensitivity over a wide range of muscle length. Inhibition of these gamma motor fiber action potentials, as provided by this embodiment, reduces the sensitivity of the muscle spindles, resulting in reduced innervation of Ia sensory fibers. As a result, the gamma motor fiber inhibition achieves an effect generally similar to that achieved by direct inhibition of Ia sensory fibers, and, for some applications, is achieved generally simultaneously therewith or in intermittent alternation therewith.

In a preferred embodiment of the present invention, control unit 20 drives electrode device 18 to apply a current that inhibits efferent action potentials traveling in at least one alpha motor fiber 44 or alpha motor fiber 46 innervating muscle 14 and synergistic muscle 15, respectively. Inhibition of these alpha motor fiber action potentials, as provided by this embodiment, typically results in partial paralysis of the limb, which in turn typically reduces spasticity.

Alternatively, a single implanted system provides one or the other form of inhibition. In this embodiment, electrode device 18 preferably is applied to nerve 22 in the vicinity of muscle 14. It is to be appreciated that although a single electrode device 18 is shown in FIG. 4 for simplicity, electrodes in electrode device 18 may be placed at a variety of sites, and that electrode device 18 therefore may be distributed across a number of discrete manufactured units.

Figure 5:
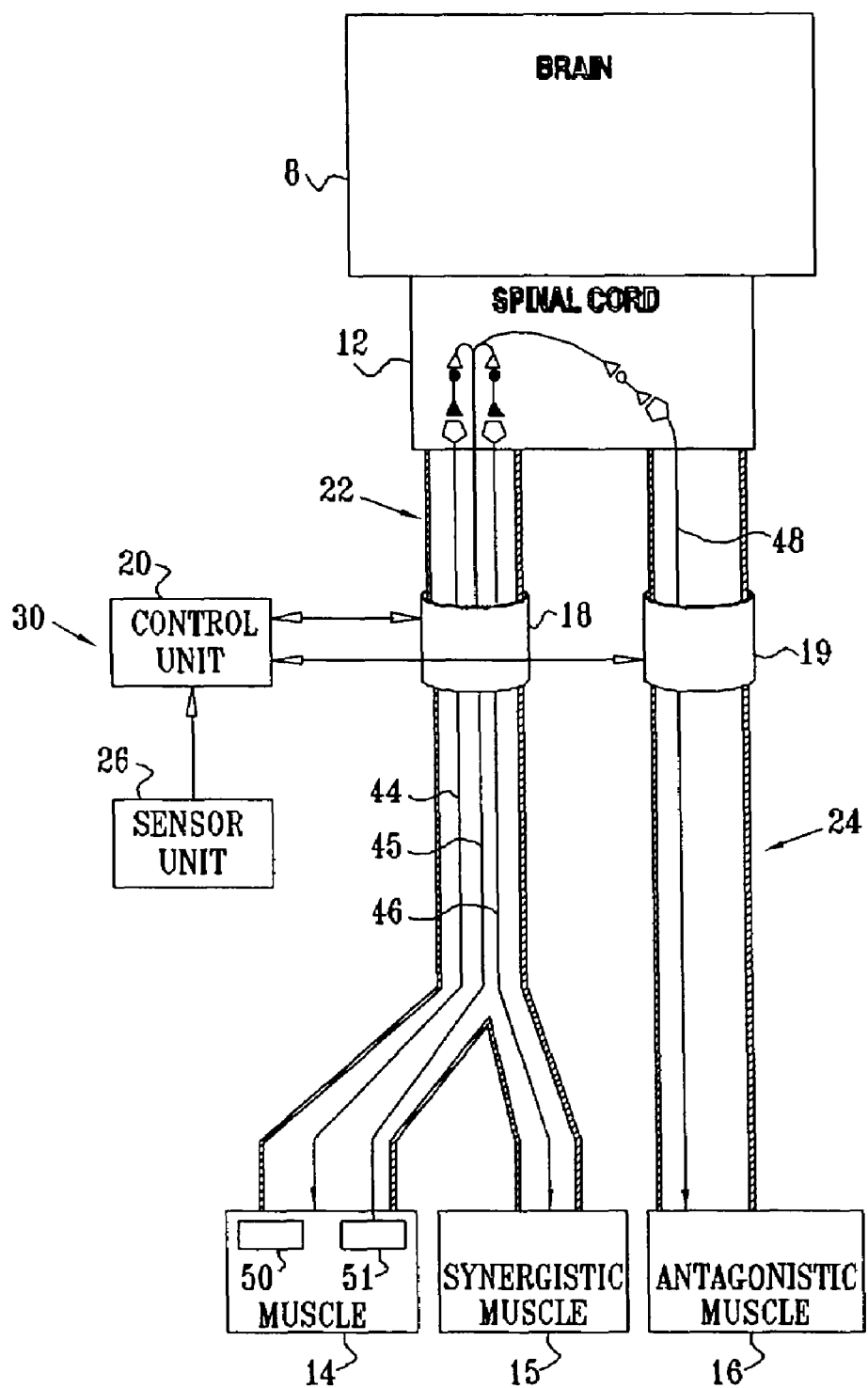
FIG. 5 is a block diagram that schematically illustrates the spasticity treatment system of FIG. 3, showing a Ib sensory fiber, in accordance with a preferred embodiment of the present invention.

FIG. 5 is a block diagram that schematically illustrates system 30 applied to nerve 22, showing at least one Ib sensory fiber 45 innervating a Golgi tendon organ 51 of muscle 14, in accordance with a preferred embodiment of the present invention. Control unit 20 drives electrode device 18 to apply a current that induces the propagation of afferent action potentials in sensory fiber 45 from Golgi tendon organ 51 to spinal cord 12. These action potentials may indirectly stimulate antagonistic muscle 16 to contract, and the action potentials may induce muscle 14 and synergistic muscles 15 to relax. By inducing contraction of antagonistic muscle 16 and relaxation of muscles 14 and 15, the application of the current compensates, at least partially, for the reduced inhibition applied to the reflex arc due to the damaged UMN or due to other causes. As a result, this treatment achieves an effect generally similar to that achieved by inhibition of Ia sensory fibers, thereby typically reducing spasticity of the extensor/flexor muscle pair. Although the fibers leading to muscle 14 and synergistic muscle 15, on the one hand, and to antagonistic muscle 16, on the other hand, are shown in FIG. 5 as contained in separate nerves, some or all of these fibers are sometimes contained within a single nerve bundle, or in separate nerve bundles within a single nerve.

Reference is again made to FIG. 4. In a preferred embodiment of the present invention for treating muscle weakness, control unit 20 drives electrode device 18 to:

apply a current that (a) inhibits propagation of afferent action potentials traveling from muscle spindle 50 to spinal cord 12 in sensory fiber 40, and/or (b) inhibits propagation of efferent action potentials traveling from spinal cord 12 in gamma motor fiber 42; and apply a current that (a) stimulates action potentials in alpha motor fiber 44 and/or alpha motor fiber 46, and/or (b) directly stimulates muscle 14 and/or synergistic muscle 15, as opposed to a nerve that innervates the muscle. Alternatively, two separate electrode devices are used for applying the respective inhibiting and stimulating currents. Preferably sensory fiber 40 includes at least one Ia sensory fiber. Alternatively, one or more A-beta motor fibers (not shown) are stimulated instead of or in addition to alpha motor fibers 44 and/or 46. As a result of the muscle stimulation, muscle strength, which was reduced by spinal cord pathology, is at least partially restored. At the same time, inhibition of the sensory fibers moderates the reflex arc, thereby reducing spasticity, as described above. Preferably, but not necessarily, electrode device 18 is applied to the nerve as close as possible to muscles 14 and 15 before nerve 22 splits into multiple branches. Alternatively, the electrode device is applied to the nerve generally close to the spinal cord. Preferably, the motor fibers are stimulated using techniques such as those described in the above-cited US patent application entitled, "Electrode assembly for nerve control," to Gross et al., filed Jul. 24, 2002, which is assigned to the assignee of the present patent application and is incorporated herein by reference. When such techniques are used, typically A-beta fibers are stimulated in order to stimulate finely-controlled movements, while both A-beta fibers and alpha fibers are stimulated together in order to produce stronger movements.

Figure 6:
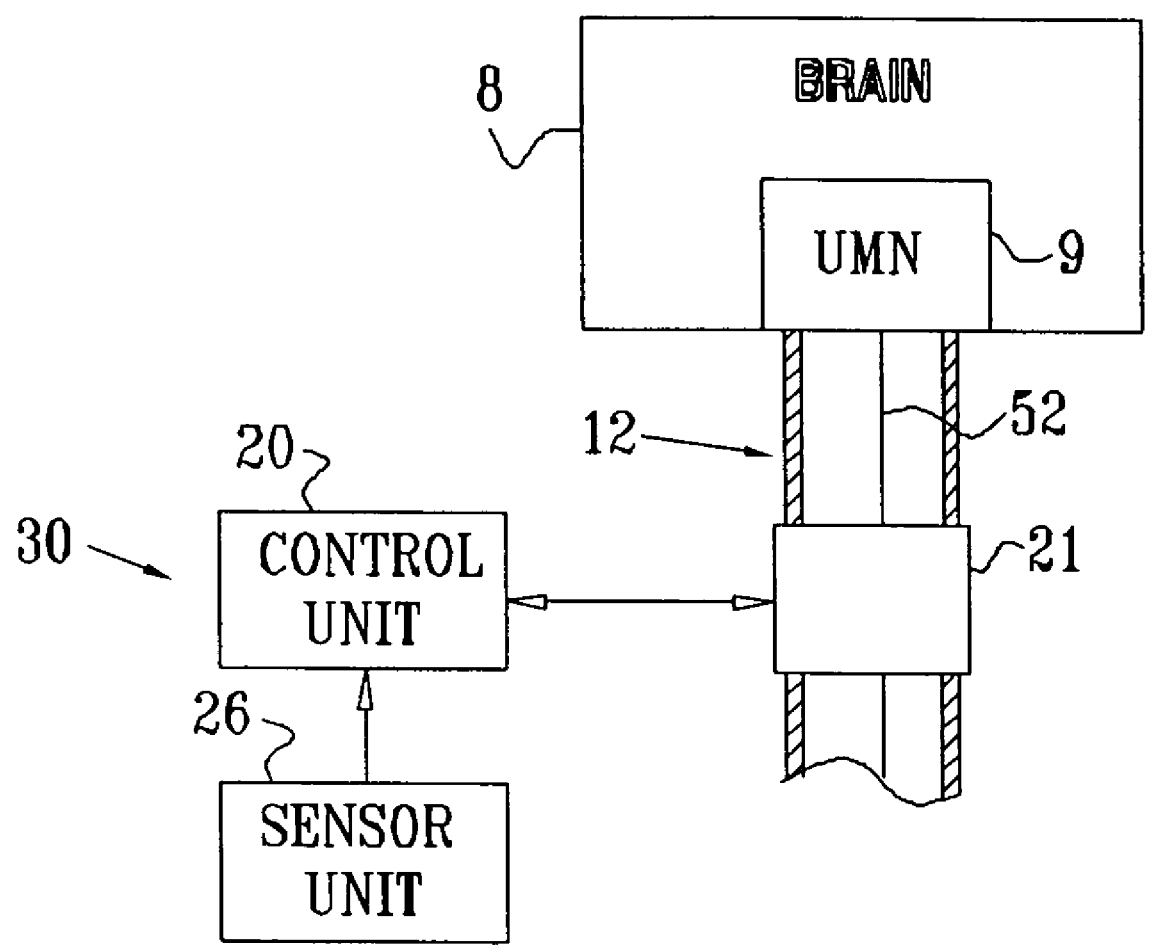
FIG. 6 is a block diagram that schematically illustrates the spasticity treatment system of FIG. 3 applied to fibers descending from an upper motor neuron (UMN) of a subject, in accordance with a preferred embodiment of the present invention.

FIG. 6 is a block diagram that schematically illustrates system 30 applied to fibers 52 descending from an upper motor neuron (UMN) 9 of subject 10, for treating spasticity and/or muscle weakness, in accordance with a preferred embodiment of the present invention. An electrode device 21 is applied in a vicinity of a nerve tract of spinal cord 12 which includes fibers 52, and control unit 20 drives electrode device 21 to apply a current so as to stimulate fibers 52. In the case of a subject with a spinal cord injury, electrode device 21 is preferably applied to the spinal cord below the level of the injury. The stimulation applied by electrode device 21 generates efferent action potentials in UMN fibers 52. These action potentials typically have generally the same effect as action potentials generated naturally in undamaged UMN fibers, which is to inhibit alpha motor neurons that innervate skeletal muscles. As a result, the exaggerated reflex arc associated with spasticity is at least partially inhibited. Preferably, electrode device 21 comprises an array of microelectrodes that are applied to the nerve tract in the spinal cord which includes fibers 52. Most preferably, techniques described in Agnew WF et al., "Microstimulation of the lumbosacral spinal cord," Huntington Medical Research Institutes Neurological Research Laboratory, Sep. 30, 1995-Sep. 29, 1998, which is incorporated herein by reference, are used to perform the microstimulation. Alternatively, electrode device 21 is applied to the surface of the spinal cord.

Preferably, control unit 20 comprises circuitry which regulates the magnitude, frequency, and/or duration of the electric field generated by individual electrodes within the electrode devices, and/or which regulates the target number of fibers to be inhibited and/or stimulated. This regulation is preferably performed in real time by utilizing a function, the inputs of which include one or more constants and/or physiological parameters measured in real time. Optionally, the constants are pre-set for a given condition. The physiological parameters are preferably indicative of the onset or strength of spastic muscle contraction and/or limb movement. For some applications, control unit 20 drives the electrode device to apply a current in a series of pulses. Alternatively or additionally, this regulation is performed responsive to a time of day, preferably determined using a clock. Further alternatively or additionally, this regulation is performed responsive to a sensed parameter that indicates whether the subject is sleeping (e.g., responsive to a substantial and prolonged reduction in motion and/or responsive to electroencephalographic recordings indicative of sleep).

For measuring the physiological parameters, system 30 preferably comprises a sensor unit 26. Sensor unit 26 preferably comprises one or more of the following:

an implanted or external electromyographic (EMG) monitor, which measures electrical activity of one or more of muscles 14, 15 and 16;

a strain gauge, which measures mechanical strain of one or more of muscles 14, 15 and 16;

an accelerometer, which measures motion and/or acceleration of limb 28; and one or more of electrode devices 18, 19 and 21, which are additionally adapted to measure action potentials in nerve fibers, such as nerve fibers 40, 42, 45, 46, and 48, and/or other nerve fibers. For example, electrode device 18 may measure action potentials in sensory fiber 40 as an indication of contraction of muscle 14.

Preferably, control unit 20 uses a feedback system to continuously analyze the outputs of sensor unit 26, so as to determine to what extent the contractions and/or movement have been reduced in response to the current applied by the one or more electrode devices. Parameters of the applied signals are preferably modified in real time, responsive to the sensor signals, until the indications of contraction and/or movement are reduced or substantially eliminated.

A variety of apparatus for unidirectionally inhibiting and inducing propagation of action potentials in nerve fibers are known in the art, some of which are described in the references cited in the Background section of the present patent application and may be adapted for use with preferred embodiments of the present invention. In addition, techniques described in a US patent application to Gross et al., entitled, "Electrode assembly for nerve control," filed Jul. 24, 2002, may be adapted for use in carrying out embodiments of the present invention. This Gross et al. application is assigned to the assignee of the present patent application and is incorporated herein by reference.

Figure 7A:
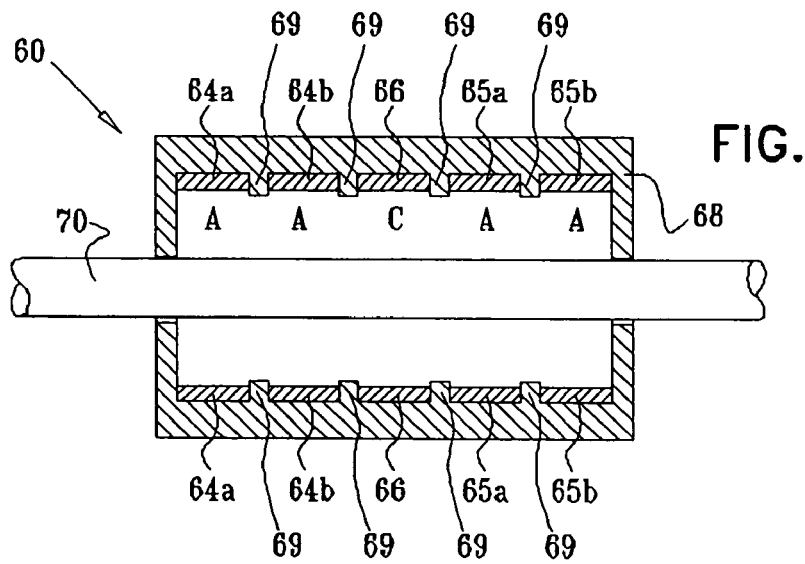
FIG. 7A is a simplified cross-sectional illustration of a multipolar electrode assembly applied to a nerve, in accordance with a preferred embodiment of the present invention.
Figure 7B:
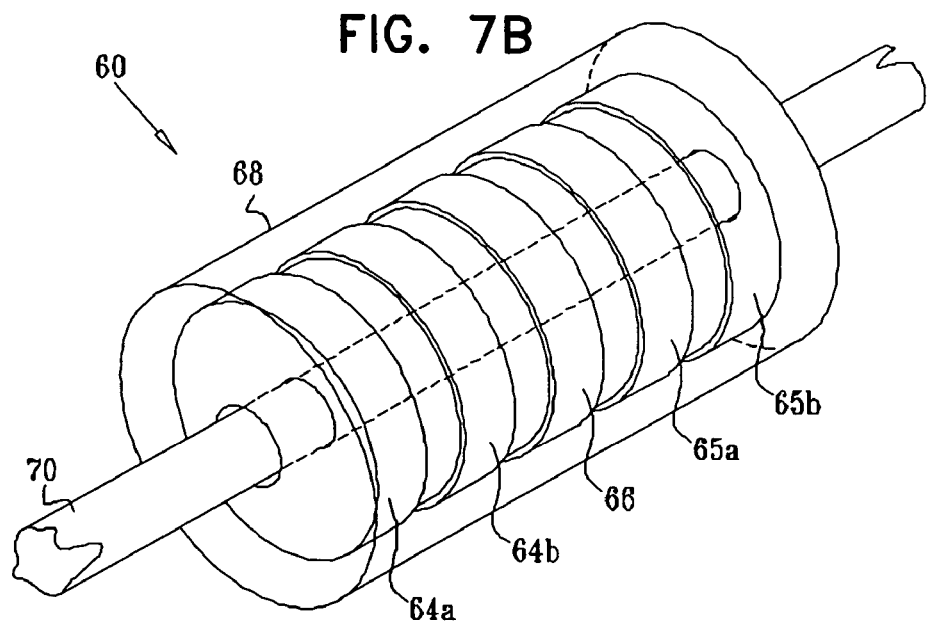
FIG. 7B is a simplified perspective illustration of the electrode assembly of FIG. 7A.

Reference is now made to FIGS. 7A and 7B. FIG. 7A is a schematic, cross-sectional illustration of an electrode assembly 60 suitable for use as electrode device 18 and/or 19 for applying current to a nerve 70, such as nerve 22 or 24, in accordance with a preferred embodiment of the present invention. FIG. 7B is a schematic pictorial illustration of electrode assembly 60, in accordance with a preferred embodiment of the present invention. It is noted that although the various electrode assemblies shown in the figures generally contain cylindrical configurations of their elements, other geometrical configurations, such as non-rotationally symmetric configurations, are also suitable for applying the principles of the present invention. In particular, a housing 68 of the electrode assembly (and the electrodes themselves) may form a complete circle around the nerve, or it may define an arc between approximately 0 and 90 degrees, between 90 and 180 degrees, between 180 and 350 degrees, or between 350 and 359 degrees around the nerve.

Preferably, electrode assembly 60 comprises a cathode 66, a primary inhibiting anode 65a, and a secondary inhibiting anode 65b, disposed so that primary inhibiting anode 65a is located between secondary inhibiting anode 65b and cathode 66. Each of these electrodes is fixed within housing 68 of the electrode assembly. Insulating elements 69, which are typically either part of the body of the housing or affixed thereto, are preferably placed so as to separate the electrodes, and to guide current from one of the electrodes towards the nerve prior to being taken up by another one of the electrodes. Preferably (as shown), the insulating elements are closer to nerve 70 than are the electrodes. Alternatively (not shown), insulating elements 69 are generally flush with the faces of the electrodes.

Typically, cathodic current driven through cathode 66 by control unit 20 stimulates fibers within nerve 70 to generate action potentials which travel in both directions within the nerve—i.e., towards anodes 65a and 65b ("the anodal direction"), and in the opposite direction, out of housing 68, towards a target ("the target direction"). Anodal current driven through anode 65a, by contrast, is typically applied so as to inhibit the action potentials which were induced by the cathodic current, and which subsequently traveled in the anodal direction.

For most applications, current applied by secondary inhibiting anode 65b is of lower magnitude than the current applied by primary inhibiting anode 65a. In this manner, the "virtual cathode" effect induced by the primary anodal current is minimized. In accordance with a preferred embodiment of the present invention, application of the primary and secondary anodal currents in appropriate ratios is configured to generally minimize the virtual cathode effect. Typically, but not necessarily, the ratio of the primary to the secondary anodal current ranges from 2:1 to 10:1.

Electrode assembly 60 preferably further comprises a primary fiber-selection anode 64b, adjacent to cathode 66 and on the other side of the housing from anodes 65a and 65b. The current applied by cathode 66 typically induces bi-directional action potential propagation in fibers in nerve 70 having a range of diameters. In order to block propagation past anode 64b of those action potentials traveling in relatively larger fibers, the primary fiber-selection anode is preferably driven to apply anodal current configured to block action potential propagation in these larger fibers of nerve 70, and configured not to block action potential propagation in the smaller fibers. In particular, since the larger fibers are generally more sensitive to being blocked by a lower level of anodal current than are the smaller fibers, a given level of current applied through fiber-selection anode 64b typically blocks action potentials in the larger fibers, while allowing passage of action potentials induced by the current from cathode 66 and traveling in the small fibers. Therefore, action potentials induced by the cathode continue to propagate in the smaller fibers, past primary fiber-selection anode 64b, out of housing 68, and towards a target site. By increasing the current driven through the primary fiber-selection anode, progressively smaller fibers are inhibited from propagating action potentials. Conversely, by decreasing the application of current through primary fiber-selection anode 64b, larger fibers are able to propagate action potentials.

For applications in which the current applied through primary fiber-selection anode 64b is sufficient to create a substantial virtual cathode effect, a secondary fiber-selection anode 64a is preferably incorporated into electrode assembly 60, adjacent to the primary fiber-selection anode and on the far side of cathode 66. In a fashion analogous to that described hereinabove with respect to secondary inhibiting anode 65b, secondary fiber-selection anode 64a is preferably driven to apply a current to the nerve smaller than that applied by primary fiber-selection anode 64b, so as to counteract the virtual cathode effect which would otherwise, in some circumstances, induce action potential propagation responsive to the current applied by primary fiber-selection anode 64b. Advantageously, use of these techniques for stimulating fibers having diameters less than a variable threshold provides the control unit with the ability to produce generally smooth recruitment of nerve fibers, and, therefore, the ability to produce generally smooth recruitment of muscle activity in muscles innervated by nerve 70.

Preferably, embodiments of the present invention for treating muscle weakness, described hereinabove with reference to FIG. 4, utilize the fiber-selection techniques described hereinabove with reference to FIGS. 7A and 7B. Fiber-selection anode 64b, and, optionally, fiber-selection anode 64a, are used to block induced efferent action potentials in larger fibers, but allow induced efferent action potentials in motor fibers, which are generally smaller, to pass.

A variety of methods for unidirectionally inhibiting and inducing propagation of action potentials are known in the art, some of which are described in the references cited in the Background section of the present patent application and may be adapted for use with preferred embodiments of the present invention.

In a preferred embodiment of the present invention, unidirectional inhibition is achieved using collision blocking, as is known in the art. For example, in order to block an action potential traveling from muscle 14 to spinal cord 12 in sensory fiber 40, unidirectional action potentials are generated by electrode device 18 to travel towards muscle 14. These electrode-generated action potentials collide with, and thereby block, the action potentials generated by muscle spindle 50 and traveling in sensory fiber 40. Preferably, electrode device 18 comprises electrode assembly 60, so as to block the unwanted afferent propagation of action potentials generated by the catheter of electrode device 18. Alternatively, high frequency blocking is used for inhibition, whereby high frequency (e.g., 600 Hz) stimulations are used to block the transmission of the action potentials through the nerve fibers.

Figure 8:
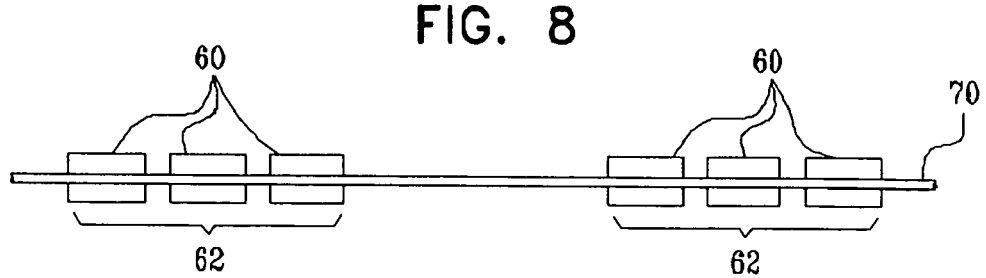
FIG. 8 is a schematic illustration of an array of electrode devices for selectively blocking the propagation through certain nerve fibers of body-generated action potentials, in accordance with a preferred embodiment of the present invention.

FIG. 8 schematically illustrates an array of electrode devices 60 for selectively blocking the propagation through certain nerve fibers of body-generated action potentials, in accordance with a preferred embodiment of the present invention. In this embodiment, inhibition of action potential propagation preferably is induced using the electrode device described hereinabove with reference to FIGS. 7A and 7B and, further, using methods disclosed in the above-cited PCT Patent Publication 02/58782 and US Patent Application Publication 2002-0099419 corresponding to U.S. patent application Ser. No. 09/824,682, entitled "Method and apparatus for selective control of nerve fibers," to Cohen and Ayal, which are assigned to the assignee of the present patent application and are incorporated herein by reference.

In this embodiment, a plurality of electrode devices 18, such as electrode assemblies 60, are applied to nerve 70, such as nerve 22 or 24. Electrode assemblies 60 are grouped together in one or more small groups 62, which are spaced at intervals along nerve 70. Control unit 20 drives the electrode assemblies to:

(a) selectively suppress the propagation of naturally-generated action potentials which propagate in a predetermined direction at a first conduction velocity through a first group of nerve fibers in nerve 70, while (b) avoiding unduly suppressing the propagation of naturally-generated action potentials propagated in the predetermined direction at a second conduction velocity through a second group of nerve fibers in nerve 70.

As described above, each electrode assembly 60 is capable of inducing, when actuated, unidirectional "electrode-generated" action potentials, which produce collision blocks with respect to the naturally-generated action potentials propagated through the first group of nerve fibers. Moreover, each electrode device is actuated in sequence, with inter-device delays timed to generally match the second conduction velocity and to thereby produce a wave of anodal blocks, which: (a) minimizes undesired blocking of the naturally-generated action potentials propagating through the second group of nerve fibers, while (b) maximizing desired blocking of the naturally-generated action potentials propagating through the first group of nerve fibers.

These techniques (as described in detail in the above-cited PCT Patent Publication 02/58782 and US Patent Application Publication 2002-0099419 corresponding to U.S. patent application Ser. No. 09/824,682) are particularly suitable in the treatment of spasticity using the techniques described herein, as the spasticity treatments described herein frequently utilize selective inhibition of certain fibers that typically have characteristic diameters that distinguish them from other fibers in the same nerve.

Alternatively or additionally, embodiments of the present invention induce the propagation of unidirectional action potentials using techniques described in the above-cited U.S. Pat. No. 4,649,936 to Ungar et al., and U.S. Pat. No. 4,608,985 to Crish et al., which describe apparatus and methods for selectively blocking action potentials passing along a nerve trunk. Further alternatively or additionally, methods and/or apparatus described in the above-cited U.S. Pat. Nos. 5,199,430 and 4,628,942 are used, possibly in combination with methods and apparatus described hereinabove.

Further alternatively or additionally, techniques described herein are practice in accordance with anodal blocking, where the anodal blocking is used to inhibit nerve fibers, whereby nerve fibers are locally hyperpolarized by anodal current, as is known in the art. By sufficiently hyperpolarizing the fibers, propagation of action potentials through the hyperpolarized zone is blocked.

Advantageously, use of the methods described hereinabove enables the selective stimulation or inhibition of desired nerve fibers based on the diameter of desired fibers.

It is to be understood that although many preferred embodiments of the present invention are described herein with respect to treating spasticity and/or muscle weakness, these techniques may also be applied, mutatis mutandis, to treating tremor. For example, sensor 26 may comprise an accelerometer and/or an electrode, and may be coupled to limb 28 and enabled to generate signals indicative of the onset of tremor. Preferably, electrode device 18 applies inhibiting and/or stimulating signals to one or more nerve fibers, as described hereinabove, which signals are configured to reduce or eliminate the detected tremor. A feedback system of control unit 20 is typically operative to continuously analyze the outputs of sensor unit 26, so as to determine to what extent the tremor has been reduced in response to the electrical stimulation by the electrode device. Parameters of signals applied by the electrode device are preferably modified in real time, responsive to signals from sensor 26, until the indications of tremor are reduced or substantially eliminated.

Alternatively or additionally, the techniques described herein are applied for treating tremor, optionally in combination with techniques described in the above-cited U.S. patent application Ser. No. 09/843,334, filed Apr. 26, 2001, entitled, "Actuation and control of limbs through motor nerve stimulation," and/or in combination with techniques known in the art.

It is to be understood that although only some preferred embodiments of the present invention have been specifically described herein with respect to treating muscle weakness, techniques of other preferred embodiments of the present invention that are described herein with respect to treating spasticity, may also be applied, mutatis mutandis, to treating muscle weakness.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   selecting a subject who suffers from spasticity;
   driving a first current into a first nerve of the subject that includes one or more sensory fibers;
   treating the spasticity by configuring the first current so as to inhibit propagation of first action potentials in one or more of the first sensory fibers;
   driving a second current into a second nerve of the subject that innervates a second muscle of the subject that is antagonistic to a first muscle innervated by at least one of the first sensory fibers, the second nerve including one or more second sensory fibers; and
   configuring the second current so as to inhibit propagation of second action potentials in at least one of the second sensory fibers.

2. A method according to claim 1, wherein the first nerve and the second nerve are the same nerve, and the first and second sensory fibers are distinct, and wherein driving the second current comprises driving the second current into the first nerve.

3. A method according to claim 1, wherein the first and second nerves comprise two distinct nerves of the subject.

4. A method, comprising:
selecting a subject who suffers from spasticity;
driving a first current into a first nerve of the subject that includes one or more sensory fibers;
treating the spasticity by configuring the first current so as to inhibit propagation of first action potentials in one or more of the first sensory fibers;
driving a second current into a second nerve of the subject that innervates a second muscle of the subject that is synergistic to a first muscle innervated by at least one of the first sensory fibers, the second nerve including one or more second sensory fibers; and
configuring the second current so as to inhibit propagation of second action potentials in at least one of the second sensory fibers.

5. A method according to claim 4, wherein the first nerve and the second nerve are the same nerve, and the first and second sensory fibers are distinct, and driving the second current comprises driving the second current into the first nerve.

6. A method according to claim 4, wherein the first and second nerves comprise two distinct nerves of the subject.

7. A method, comprising:
selecting a subject who suffers from spasticity;
driving a first current into a first nerve of the subject that includes one or more sensory fibers;
treating the spasticity by configuring the first current so as to inhibit propagation of first action potentials in one or more of the first sensory fibers;
driving a second current into a second nerve of the subject that includes one or more gamma motor fibers innervating a muscle spindle of the subject; and
configuring the second current so as to inhibit propagation of second action potentials in at least one of the gamma motor fibers.

8. A method according to claim 7, wherein the first nerve and the second nerve are the same nerve, and the first and second sensory fibers are distinct, and driving the second current comprises driving the second current into the first nerve.

9. A method according to claim 7, wherein the first and second nerves comprise two distinct nerves of the subject.

* * * * *

UNITED STATES PATENT AND TRADEMARK OFFICE
CERTIFICATE OF CORRECTION

PATENT NO. : 7,324,853 B2  Page 1 of 1
APPLICATION NO. : 10/981939
DATED : January 29, 2008
INVENTOR(S) : Shai Ayal et al.

It is certified that error appears in the above-identified patent and that said Letters Patent is hereby corrected as shown below:

Title page, item (63) correct the following:

(a) Continuation-in-part of application No. 09/843,334, filed on Apr. 26, 2001. (b) Continuation of application No. 10/254,024 filed on Sep. 24, 2002, now Pat. No. 6,892,098, which is a continuation-in-part of application No. 10/205,474, filed on Jul. 24, 2002, now Pat. No. 6,907,295, which is a continuation-in-part of application No. PCT/IL02/00068, filed Jan. 23, 2002, which is a continuation-in-part of application No. 09/944,913, filed on Aug. 31, 2001, now Patent No. 6,684,105.

Signed and Sealed this

Twenty-third Day of March, 2010

David J. Kappos
*Director of the United States Patent and Trademark Office*